(12) United States Patent
Hori et al.

(10) Patent No.: US 7,710,562 B2
(45) Date of Patent: May 4, 2010

(54) ATOMIC ANALYZER

(75) Inventors: Masaru Hori, Aichi (JP); Masafumi Ito, Wakayama (JP)

(73) Assignee: NU Eco Engineering Co., Ltd., Nishikamo-gun, Aichi (JP)

( * ) Notice: Subject to any disclaimer, the term of this patent is extended or adjusted under 35 U.S.C. 154(b) by 100 days.

(21) Appl. No.: 12/071,601

(22) Filed: Feb. 22, 2008

(65) Prior Publication Data
US 2008/0239312 A1    Oct. 2, 2008

(30) Foreign Application Priority Data
Mar. 26, 2007   (JP) ............................. 2007-078481

(51) Int. Cl.
*G01N 21/73*   (2006.01)
(52) U.S. Cl. ...................................... 356/316
(58) Field of Classification Search ................. 356/316
See application file for complete search history.

(56) References Cited

FOREIGN PATENT DOCUMENTS
JP   9-147790   6/1997

*Primary Examiner*—F. L Evans
(74) *Attorney, Agent, or Firm*—McGinn IP Law Group, PLLC (57) ABSTRACT

An atomic analyzer includes a plasma generator, in which a discharge gas is fed in a micro gap between a pair of electrodes to generate nonequilibrium atmospheric pressure plasma, a bias voltage controller that includes a plasma-leading electrode for leading the nonequilibrium atmospheric pressure plasma generated by the plasma generator to an object to be irradiated, the object to be irradiated with the nonequilibrium atmospheric pressure plasma is placed on the plasma-leading electrode, a bias voltage is applied between the plasma-leading electrode and the electrodes of the plasma generator to irradiate the object with the nonequilibrium atmospheric pressure plasma, and a spectrometer that analyzes atoms spectroscopically from light emitted from atomized generated by atomizing a substance composing the object to be irradiated by the nonequilibrium atmospheric pressure plasma irradiation or from light absorbed by the atomized atoms.

3 Claims, 9 Drawing Sheets

ATOMIC ANALYZER

TECHNICAL FIELD

The present invention relates to an atomic analyzer that analyzes atoms composing a substance. In particular, the present invention is effective in an atomic analyzer that identifies or quantitates atoms composing a solid component.

BACKGROUND ART

Conventionally, the quantitative determination of atoms contained in soil or sewage is required in terms of the environmental pollution. In this case, in general, soil or sewage must be subjected to pretreatment, such as drying or being dissolved in a chemical. Furthermore, the apparatuses used are large and are impossible to carry. It is therefore difficult to perform a component analysis at the site of pollution. The component analysis requires atomization of elements composing a substance. It is known that the atomization is performed by chemical methods or physical methods using a laser or plasma. In the chemical methods, because different elements require different treatments, it is difficult to measure multiple elements simultaneously. Furthermore, when a laser is miniaturized for convenience of carrying, the laser has a reduced power and low analytical sensitivity. Furthermore, a solid containing a liquid (or a solid in a liquid) requires complete vaporization of the liquid and vaporization of the solid. Direct use of a solid containing a liquid requires a higher-power laser, which is difficult to miniaturize. In particular, it is desired that the atomic analysis of a solid contained in a waste fluid be performed directly with the waste fluid. However, a portable laser cannot be used in such an analysis of a solid contained in a waste fluid.

On the other hand, a plasma generator for use in the atomic analysis using plasma is known by Patent Document 1. Patent Document 1 discloses an apparatus that generates helium plasma, which has the highest atomization capability. Since a helium gas has a very high excitation temperature, surrounding walls that generate plasma must be cooled. A helium gas may be used to cool the surrounding walls. However, helium has a high thermal conductivity and exhibits extensive thermal diffusion. If a helium gas is fed in the axial direction for cooling, therefore, the energy of helium is dissipated into the atmosphere.

According to Patent Document 1, to solve this problem, a helium gas is fed spirally into an outer discharge tube to reduce the flow rate in the axial direction, thus forming ring-shaped plasma around the axis. A gas to be analyzed is supplied into the ring-shaped plasma.

[Patent Document 1] Japanese Unexamined Patent Application Publication No. 9-147790

DISCLOSURE OF THE INVENTION

Problems to be Solved by the Invention

However, in the apparatus disclosed in Patent Document 1, a sample gas is supplied in parallel with a discharge gas flow into the spirally generated plasma. Thus, the analytical sample is limited to gases.

Hence, the apparatus disclosed in Patent Document 1 cannot be used to analyze component atoms contained in soil, sludge, or waste fluid containing metallic elements to be analyzed.

Accordingly, it is an object of the present invention to provide a portable atomic analyzer that can produce atoms from soil, sludge, waste fluid, or another sample containing metallic elements to be analyzed and can spectroscopically analyze the atoms.

Means for Solving the Problems

A first invention is an atomic analyzer that includes a plasma generator in which a discharge gas is fed in a micro gap between a pair of electrodes to generate nonequilibrium atmospheric pressure plasma, a bias voltage controller that includes a plasma-leading electrode for leading the nonequilibrium atmospheric pressure plasma generated by the plasma generator to an object to be irradiated, the object to be irradiated with the nonequilibrium atmospheric pressure plasma being placed on the plasma-leading electrode, a bias voltage being applied between the plasma-leading electrode and the electrodes of the plasma generator to irradiate the object with the nonequilibrium atmospheric pressure plasma, and a spectrometer that analyzes the atoms spectroscopically from light emitted from atomized atoms generated by atomizing a substance composing the object to be irradiated by the nonequilibrium atmospheric pressure plasma irradiation or from light absorbed by the atomized atoms.

A discharge gas is fed a micro gap between a pair of electrodes applied high-voltage, thus forming nonequilibrium atmospheric pressure plasma between the electrodes. Examples of the discharge gas include argon, nitrogen, helium, and air. Since the distance between the electrodes is small, the discharge can be concentrated in confined space between the electrodes, thus forming nonequilibrium plasma under atmospheric pressure. The spectroscopic analysis may be performed by a method in which a light source is used to identify or quantitate atoms from absorption characteristics or by emission spectrometry, that is, a method in which the emission spectrum of atomized atoms is analyzed to identify or quantitate the atoms.

The material of the electrodes of the plasma generator or the plasma-leading electrode may be stainless steel, molybdenum, or copper. Preferably, the distance between the electrodes is in the range of 0.5 to 3.0 mm.

Furthermore, a second invention is characterized in that the first invention further includes a magnetic field generator that is disposed between the plasma-leading electrode and the electrodes of the plasma generator, confines the nonequilibrium atmospheric pressure plasma emitted to the object to be irradiated, surrounds the object to be irradiated, and applies a magnetic field to the object to be irradiated.

Furthermore, a third invention is characterized in that, in the second invention, the flow direction of the nonequilibrium atmospheric pressure plasma emitted to the object to be irradiated is altered by a magnetic field generated by the magnetic field generator so that the direction of radiation of the nonequilibrium atmospheric pressure plasma is different from the flow direction of the discharge gas.

ADVANTAGES OF THE INVENTION

According to the first invention, nonequilibrium atmospheric pressure plasma can be generated easily, and a bias voltage applied between the plasma-leading electrode and the electrodes of the plasma generator allows the object to be irradiated with the plasma stably and efficiently. Consequently, even when the object to be irradiated is a solid or a solid mixed with a liquid, the solid can be atomized easily.

According to the second invention, the magnetic field generator can confine the nonequilibrium atmospheric pressure plasma emitted to the object to be irradiated, thus allowing the object to be irradiated to be atomized effectively.

According to the third invention, the magnetic field generator turns the direction of radiation of the nonequilibrium atmospheric pressure plasma emitted to the object to be irradiated toward the direction different from the flow direction of the discharge gas. The discharge gas flow therefore does not scatter the nonequilibrium atmospheric pressure plasma emitted to the object to be irradiated. Furthermore, since the object to be irradiated is not disposed in the direction of the discharge gas flow, the discharge gas flow does not scatter the object to be irradiated.

Preferred embodiments of the present invention will be described in detail below. Technical matters necessary for the practice of the present invention other than the details referred to herein may be understood as design matters by a person skilled in the art on the basis of the related art. The present invention may be practiced on the basis of the technical contents disclosed herein and common general technical knowledge in the art.

Embodiments of the present invention will be described below. However, the present invention is not limited to these embodiments, and the technical ideas contained in the embodiments define the scope of the present invention.

Embodiment 1

Figure 1:
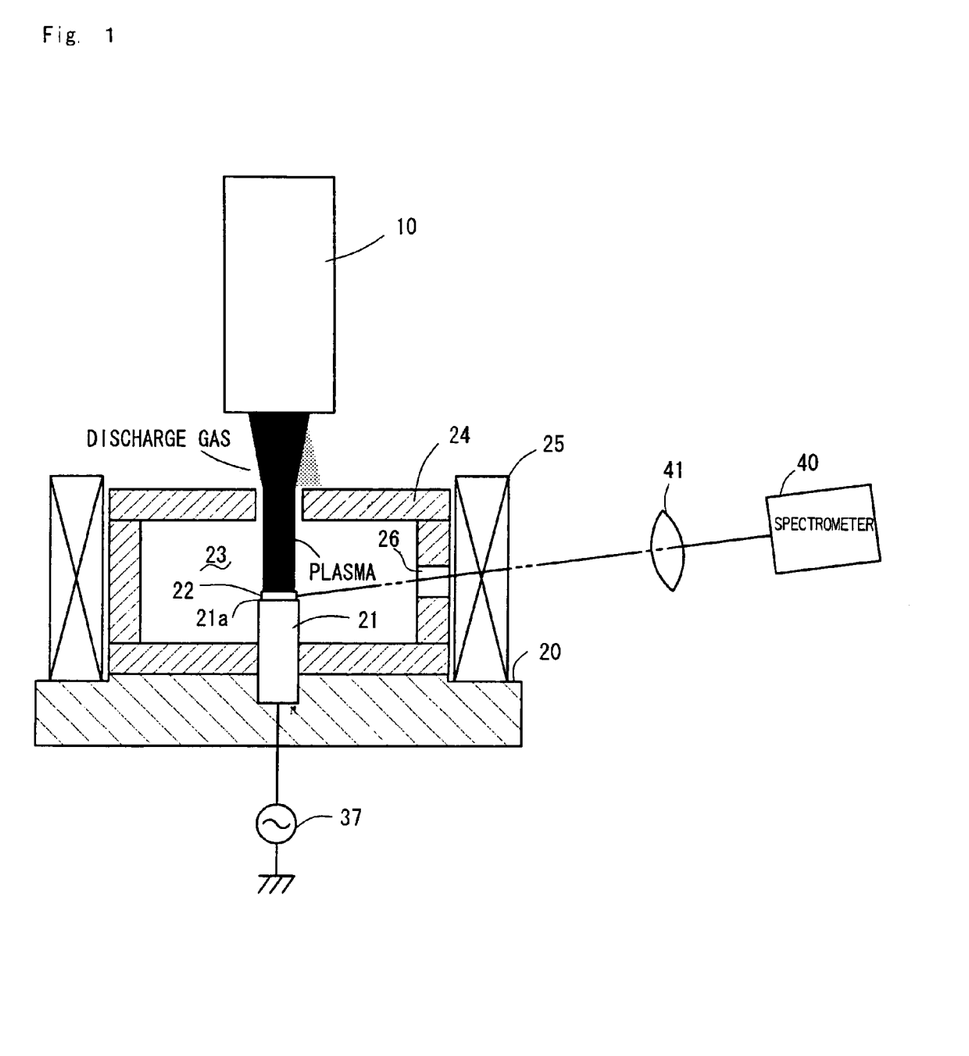
[FIG. 1] A schematic view of an atomic analyzer according to a specific embodiment of the present invention.

FIG. 1 is a schematic general view of an atomic analyzer according to a specific embodiment of the present invention. A plasma-leading electrode 21 is disposed on a base 20. An object to be irradiated 22, which is to be atomized, is disposed on the top surface 21a of the plasma-leading electrode 21. The plasma-leading electrode 21 and the object to be irradiated 22 are disposed in a cylindrical reaction chamber 23 surrounded by walls 24. A plasma generator 10 is disposed over the reaction chamber 23. The plasma generator 10 irradiates the object to be irradiated 22 with nonequilibrium atmospheric pressure plasma. A magnetic field generator 25 is disposed around the reaction chamber 23. The magnetic field generator 25 generates a magnetic flux in the direction perpendicular to the top surface 21a of the plasma-leading electrode 21. The center line of a magnetic flux generated by the magnetic field generator 25 in a cross section perpendicular to the vertical axis of the top surface 21a of the plasma-leading electrode 21 is configured to pass through the center of the top surface 21a.

Figure 2:
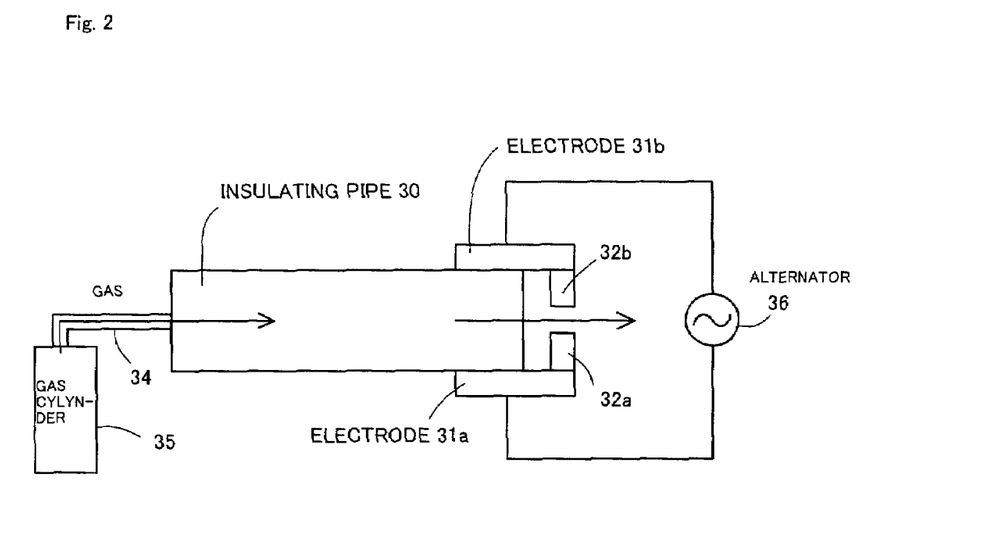
[FIG. 2] A detailed view of a plasma generator in the atomic analyzer according to the specific embodiment of the present invention.
Figure 3:
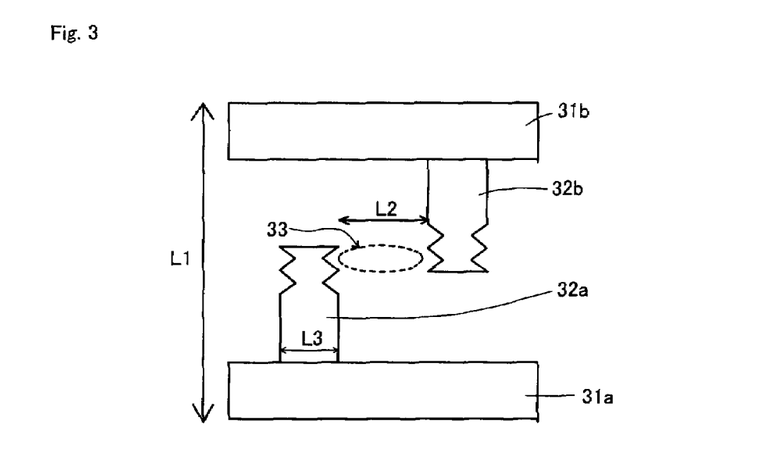
[FIG. 3] A detailed view of electrodes in the atomic analyzer according to the specific embodiment of the present invention.

The structure of the nonequilibrium atmospheric pressure plasma generator 10 will be described below. FIG. 2 illustrates the nonequilibrium atmospheric pressure plasma generator 10. The generator 10 includes an insulating pipe 30 and planar electrodes 31a and 31b. The insulating pipe 30 is coupled via piping 34 to a gas cylinder 35 containing a discharge gas. The insulating pipe 30 has an inner diameter of 0.5 mm. The inner diameter of the insulating pipe 30 is effective in the range of 0.5 to 1 mm. Parts of the electrodes 31a and 31b are in contact with an upper portion and a lower portion of an end of the insulating pipe 30 such that the electrodes 31a and 31b sandwich the insulating pipe 30. FIG. 3 is an enlarged view of the electrodes 31a and 31b, viewed from a gas outlet. Two projections 32a and 32b extend facing each other perpendicularly from portions of the electrodes 31a and 31b that are not in contact with the insulating pipe 30. A discharge gas flows between the projections 32a and 32b. The distance L1 between the electrodes 31a and 31b is 10 mm. The distance L2 between the two projections 32a and 32b is 1.0 mm. The width L3 of the projections 32a and 32b is 3 mm. The tips of the projections have a serrated edge. The serrated edge is provided to prevent the diffusion of a discharge area and reduce the discharge area. The insulating pipe is formed of ceramic.

The plasma-leading electrode 21 is a cylinder having a diameter of 2 mm and a length of 10 mm. The top surface 21a of the plasma-leading electrode 21, on which the object to be irradiated 22 is placed, has a reduced area to stabilize the plasma irradiation point. Furthermore, the electrodes 31a and 31b are formed of stainless steel, and the plasma-leading electrode 21 is formed of copper. Direct plasma irradiation of the plasma-leading electrode 21 causes its component elements to be atomized and emit light, thereby interfering with the analysis of atoms composing an object to be irradiated. To prevent the interference, the surface of the plasma-leading electrode 21 may be coated with an element material that is not contained in the object to be irradiated, or may be coated with a material that is difficult to atomize. Furthermore, the discharge gas is argon.

An alternator 36 applies a voltage between the electrodes 31a and 31b at 60 Hz. Furthermore, the electrode 31b is coupled to the earth. An alternator 36 applies a voltage between the plasma-leading electrode 21 and the electrode 31b at 60 Hz.

A window 26 is disposed in the walls 24 of the reaction chamber 23. Light emitted by the object to be irradiated 22 can be received from outside through the window 26. The wavelength of light emitted by the object to be irradiated 22 can be analyzed by a spectrometer 40 via a converging lens 41. That is, emission spectrometry that analyzes the emission spectrum of atomized atoms is performed.

EXPERIMENTAL EXAMPLE 1

With this apparatus, the electrode 31b was set to be a ground potential, an alternating voltage of 9 kV at 60 Hz was applied between the electrodes 31a and 31b, and an alternating voltage of 9 kV at 60 Hz was applied between the plasma-leading electrode 21 and the electrode 31b. An argon gas was supplied between the electrodes 31a and 31b from the insulating pipe 30 at a flow rate of 1.2 L/min. First, in the absence of a magnetic field generated by the magnetic field generator 25, the following experiment was carried out. Discharge was started between the electrodes 31a and 31b to generate argon plasma. The plasma is drawn toward the plasma-leading electrode 21, thus generating a plasma jet between the plasma-leading electrode 21 and the electrodes 31a and 31b. The generation of plasma was observed while altering the distance between the plasma-leading electrode 21 and the electrodes 31a and 31b (hereinafter referred to simply as "distance from leading electrode"). At a distance from leading electrode in the range of 2 to 10 mm, a plasma jet was stably generated between the plasma-leading electrode 21 and the electrodes 31a and 31b. At a distance from leading electrode of 16 mm or more, the plasma did not reach the plasma-leading electrode 21, and remained between the electrodes 31a and 31b.

EXPERIMENTAL EXAMPLE 2

Figure 4:
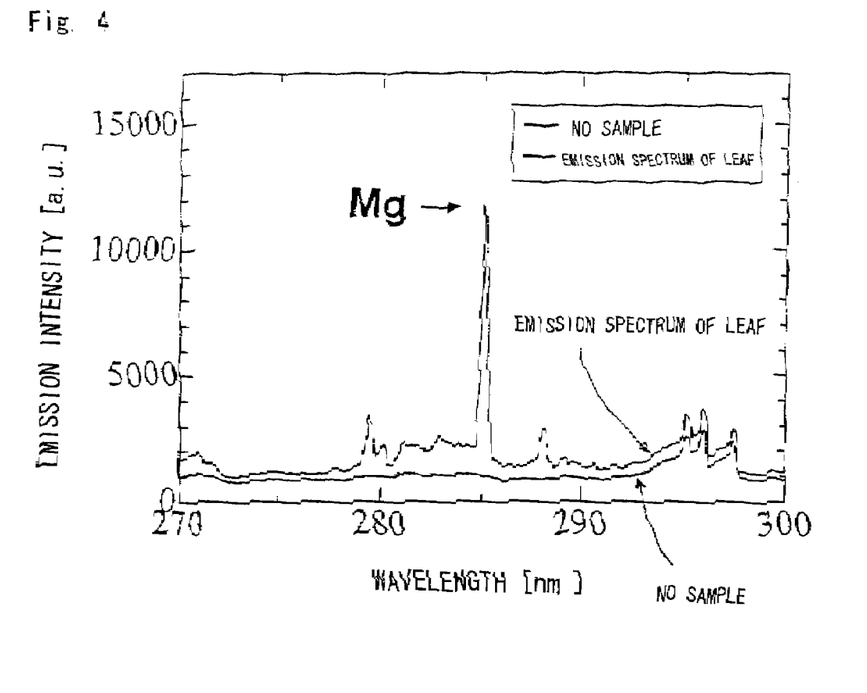
[FIG. 4] A wavelength vs. emission intensity chart of atomic analysis measurements according to Experimental Example 2, using the plasma generator according to the specific embodiment of the present invention.

A leaf containing 0.1% (1000 ppm) Mg was selected as the object to be irradiated 22. Metal atom components of the leaf were analyzed. The distance from leading electrode was set to be 6 mm such that the leaf was not in contact with the electrodes 31a and 31b, and that the plasma jet was generated stably. The flow rate of the argon gas was set to be 1.2 L/min. Light emitted by the leaf was analyzed with the spectrometer 40. FIG. 4 shows the results. FIG. 4 shows a line spectrum of from 285.1 to 285.2 nm. This line spectrum was attributed to a Mg atom. Furthermore, the excitation temperature was determined to be about 6000K from the spectrum emission intensity and the Einstein A coefficient.

EXPERIMENTAL EXAMPLE 3

Figure 5:
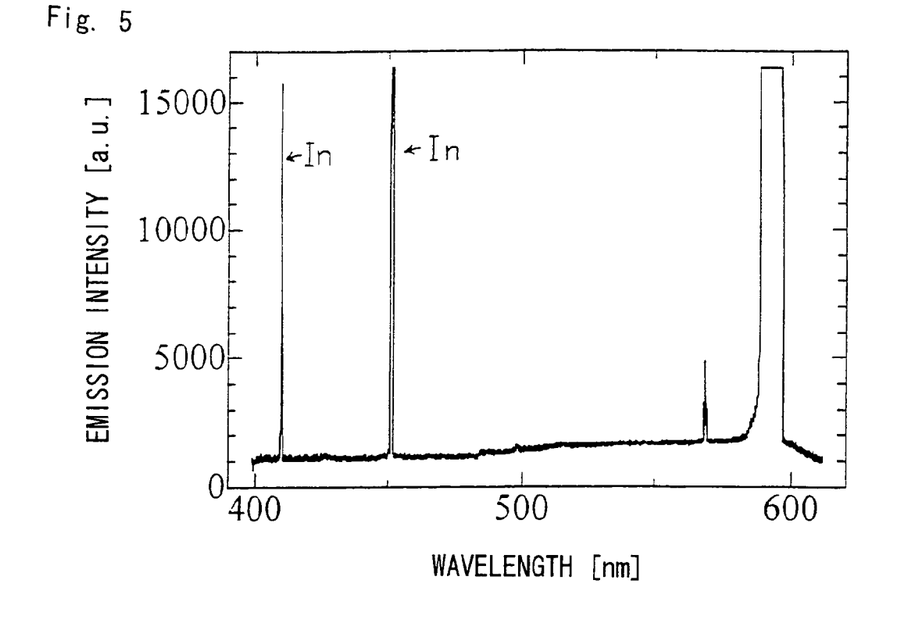
[FIG. 5] A wavelength vs. emission intensity chart of atomic analysis measurements according to Experimental Example 3, using the plasma generator according to the specific embodiment of the present invention.

The distance from leading electrode was set to be 4 mm. The flow rate of the argon gas was set to be 1 L/min. The object to be irradiated 22 was an In plate. The other conditions, including the applied voltage, were the same as in Experimental Example 2. FIG. 5 shows the measurements. Line spectra were observed at 410.2 and 451.1 nm. These are emission spectra of In.

EXPERIMENTAL EXAMPLE 4

Figure 6:
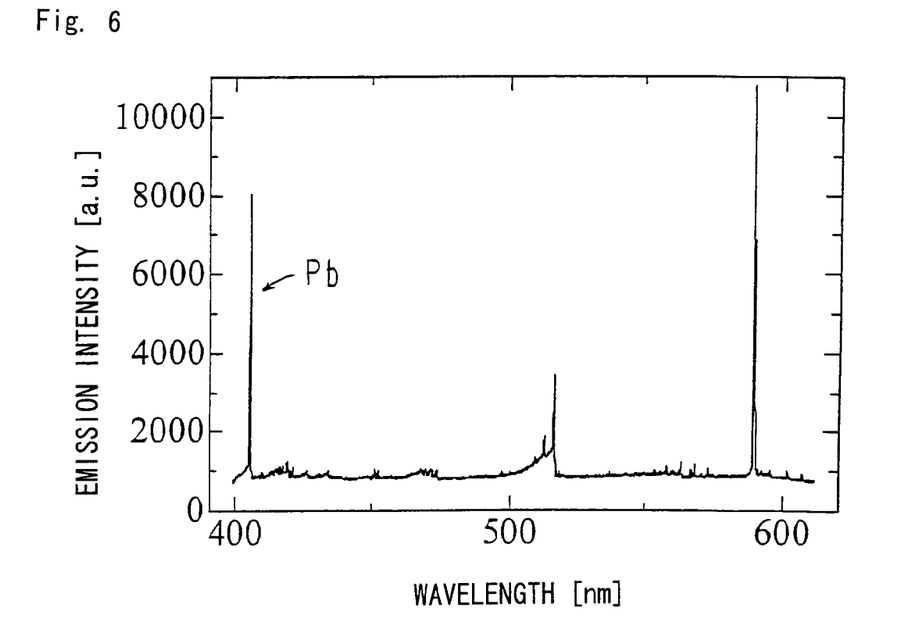
[FIG. 6] A wavelength vs. emission intensity chart of atomic analysis measurements according to Experimental Example 4, using the plasma generator according to the specific embodiment of the present invention.

The object to be irradiated 22 was solder (40% Pb and 60% Sn). The emission spectrum of Pb was observed under the same conditions as in Experimental Example 3. FIG. 6 shows the measurements. The emission spectrum of Pb was observed at 405.8 nm.

EXPERIMENTAL EXAMPLE 5

Figure 7:
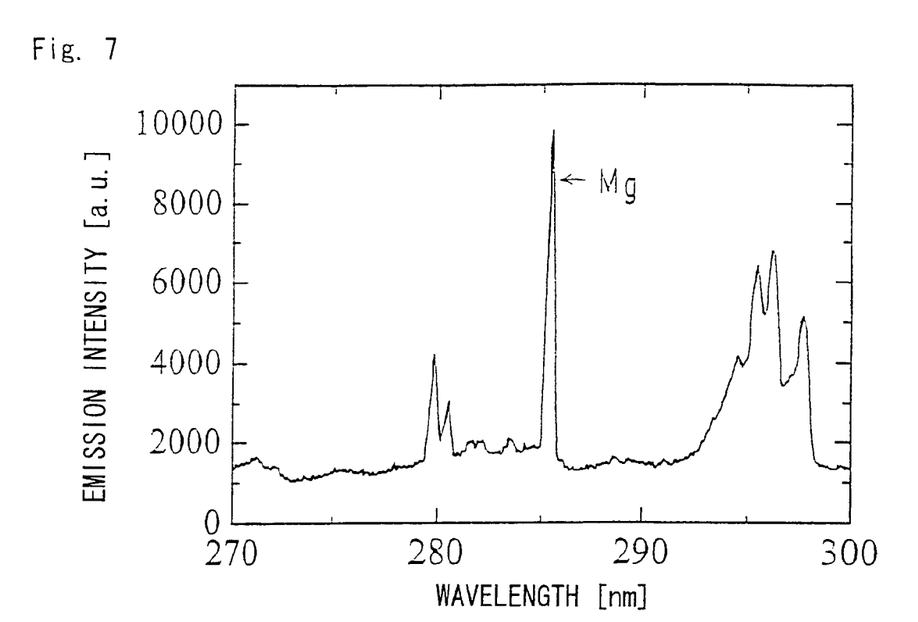
[FIG. 7] A wavelength vs. emission intensity chart of atomic analysis measurements according to Experimental Example 5, using the plasma generator according to the specific embodiment of the present invention.

A mixture of 1 mg of solid $Mg(NO_3)_2$ powder and 7 mg of water was used as the object to be irradiated 22. The experimental conditions were the same as in Experimental Example 3. FIG. 7 shows the measurements. An emission spectrum of 285.2 nm was observed. This is an emission spectrum of Mg. This demonstrates that an apparatus according to the present invention can perform atomic analysis even when the substance to be analyzed is a solid mixed with a liquid. Although it is difficult to atomize a solid mixed with a liquid by atomic absorption spectrometry with a conventional atomization apparatus, an apparatus according to the present invention can overcome this difficulty. In other words, according to the present invention, a solid pollutant in sludge or waste fluid can be identified or quantitated.

EXPERIMENTAL EXAMPLE 6

Figure 8:
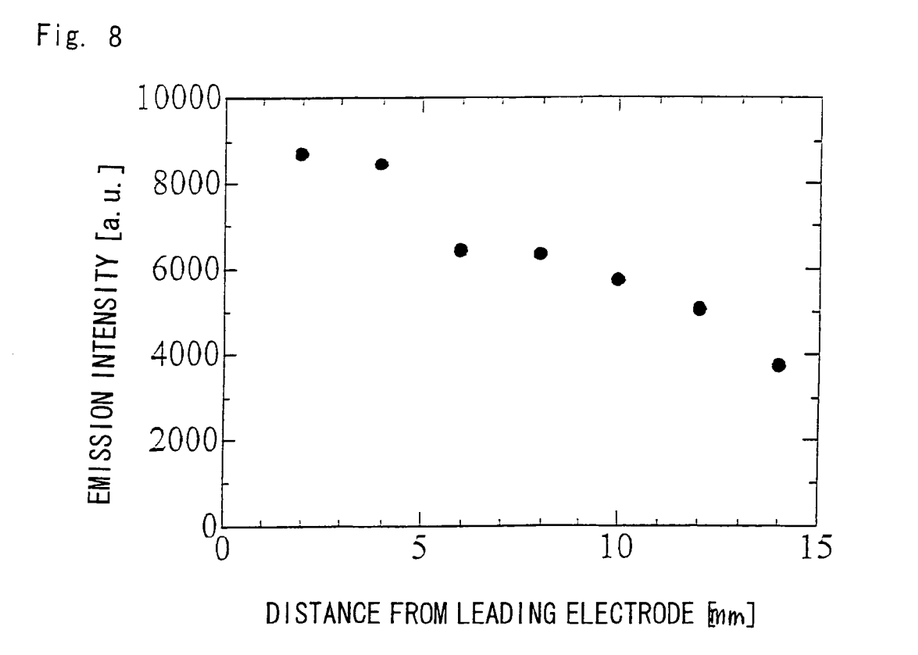
[FIG. 8] A chart of measurements of the relationship between the Mg emission intensity and the distance from leading electrode according to Experimental Example 6, using the plasma generator according to the specific embodiment of the present invention.

The relationship between the distance from leading electrode and the emission intensity of Mg spectrum was determined using a mixture of a solid $Mg(NO_3)_2$ powder and water as the object to be irradiated 22. The applied voltage and the flow rate of the argon gas were the same as in Experimental Example 3. FIG. 8 shows the measurements. The emission intensity of atomized atoms composing the object to be irradiated was at its maximum at a distance from leading electrode in the range of 2 to 4 mm. The emission intensity decreases with increasing distance from leading electrode. This is because a short distance from leading electrode results in a large electric field between the electrodes, thus providing large energy to electrons.

EXPERIMENTAL EXAMPLE 7

Figure 9:
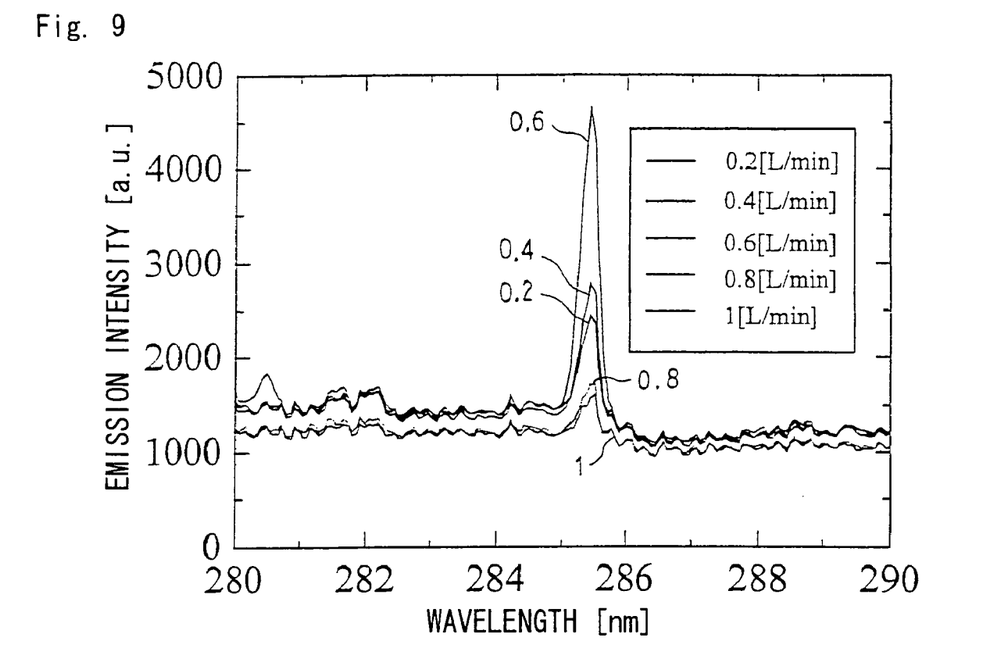
[FIG. 9] A wavelength vs. emission intensity chart with a parameter of the discharge gas flow rate according to Experimental Example 7, using the plasma generator according to the specific embodiment of the present invention.
Figure 10:
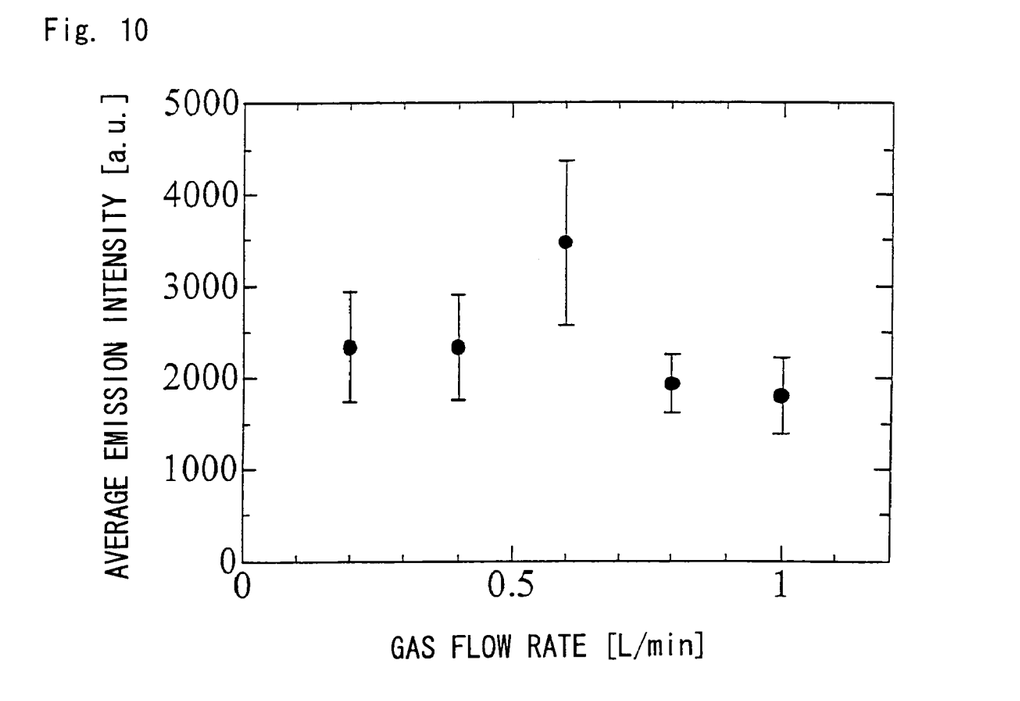
[FIG. 10] A chart of measurements of the relationship between the discharge gas flow rate and the Mg emission intensity according to Experimental Example 7, using the plasma generator according to the specific embodiment of the present invention.

The relationship between the flow rate of the argon gas and the emission intensity of Mg spectrum was determined using a mixture of a solid $Mg(NO_3)_2$ powder and water as the object to be irradiated 22. The distance from leading electrode was set to be 4 mm. The other conditions, including the applied voltage, were the same as in Experimental Example 3. FIG. 9 shows the measurements. The emission spectrum of Mg reaches maximum at a flow rate of 0.6 L/min. Furthermore, the relationship between the mean value of five measurements of the emission spectrum of Mg and the flow rate of the argon gas was determined. FIG. 10 shows the results. There is an optimum flow rate of a discharge gas.

EXPERIMENTAL EXAMPLE 8

Figure 11:
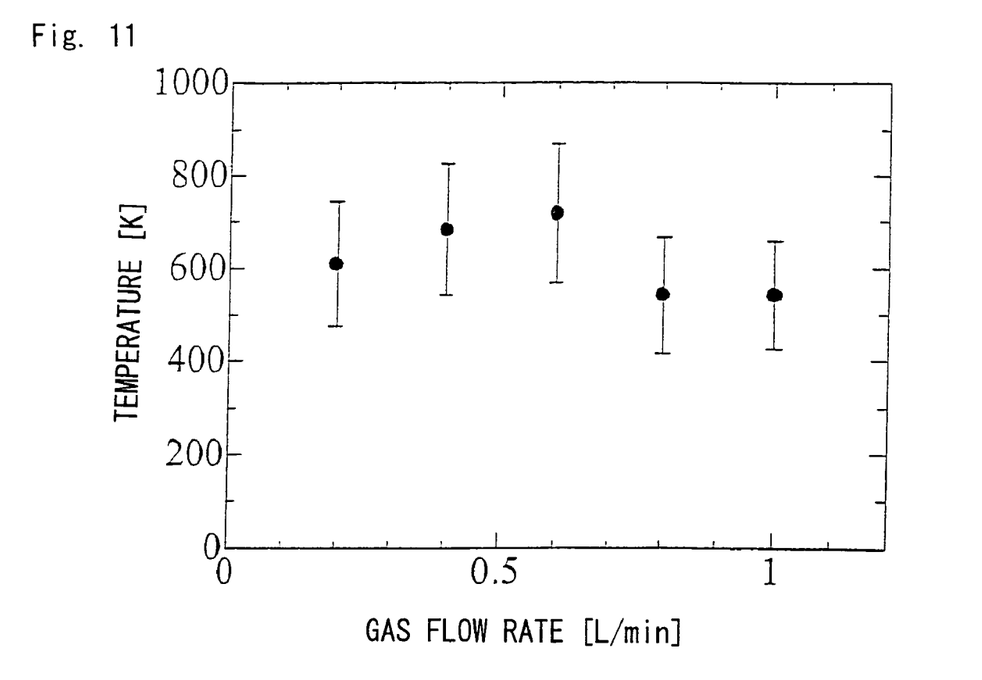
[FIG. 11] A chart of the relationship between the discharge gas flow rate and the gas temperature according to Experimental Example 8, using the plasma generator according to the specific embodiment of the present invention.

As described below, the rotational temperature of the non-equilibrium atmospheric pressure plasma was determined in the apparatus according to the present embodiment. The rotational spectrum of nitrogen molecules at 380.5 nm was determined from the plasma emission in the present embodiment. The gas temperature was calculated from the spectrum. The gas temperature of plasma was determined as a function of the flow rate of the argon gas. FIG. 11 shows the measurements. The temperature of plasma in the apparatus according to the present embodiment is as low as 400K to 900K.

With an atomizer used in conventional atomic absorption spectrometry, the plasma temperature is as high as 1850K to 4800K by flame, and is as high as 1800K to 3300K with a graphite furnace. In the present invention, high-energy electrons or ions in nonequilibrium atmospheric pressure plasma can be used to efficiently atomize the object to be irradiated.

These Experimental Examples show that plasma is stably formed between the plasma-leading electrode 21 and the electrodes 31a and 31b at a distance from leading electrode in the range of 2 to 10 mm. However, when the object to be irradiated 22 is large, the distance from leading electrode must be increased. Thus, as illustrated in FIG. 1, the magnetic field generator 25 is used to generate a magnetic flux in the direction perpendicular to the top surface 21a of the plasma-leading electrode 21. Plasma is forced to move spirally along the magnetic flux. Plasma can therefore be led to the plasma-leading electrode 21 without being scattered. This allows an increase in the distance from leading electrode. Plasma can be stably generated toward the plasma-leading electrode 21 even at a distance from leading electrode as large as about 40 mm.

Embodiment 2

Figure 12:
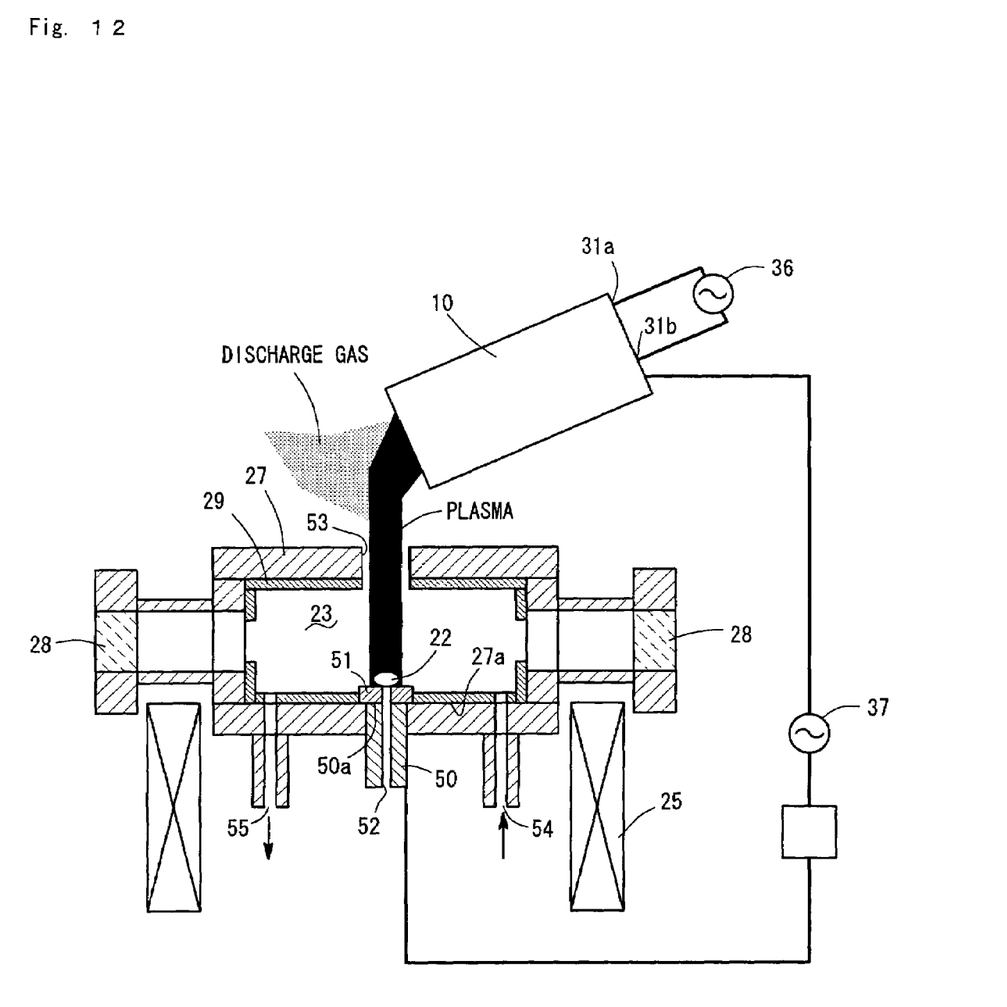
[FIG. 12] A schematic view of an atomic analyzer according to specific Embodiment 2 of the present invention.

In an apparatus according to the present embodiment, the direction of a discharge gas flow is different from the direction of a magnetic flux generated by a magnetic field generator. Components having the same function as in Embodiment 1 illustrated in FIG. 1 have the same reference numerals. The structure of a nonequilibrium atmospheric pressure plasma generator 10 is the same as in Embodiment 1. In the present embodiment, a measuring window 28 protrudes outward from a case 27 of a reaction chamber 23. The reaction chamber 23 is cylindrical. Plates 29 for preventing the adhesion of impurities are attached to the internal surface of the reaction chamber 23. The plates 29 are formed of Teflon or ceramic. The plates 29 for preventing the adhesion of impurities are detachable so that a contaminated plate can be replaced easily. Furthermore, a tubular plasma-leading electrode 50 is disposed in the bottom 27a of the case 27. A sample stage 51 having a communicating hole at the center thereof is disposed on the top surface 50a of the case 27. The sample stage 51 may be formed of an insulator, such as silicon oxide, aluminum oxide, silicon nitride, or Teflon, or a semiconductor, such as Si or GaAs. An object to be irradiated 22 is placed on the sample stage 51. A through-hole 52 is disposed along the central axis of the sample stage 51 and the plasma-leading electrode 50. The object to be irradiated 22 is introduced through the through-hole 52.

The center line of a magnetic flux generated by a magnetic field generator 25 in a cross section perpendicular to the through-hole 52 passes through the through-hole 52, and is perpendicular to a mounting surface of the sample stage 51 disposed on the top surface 50a of the plasma-leading electrode 50. This perpendicular direction is hereinafter referred to as the direction of magnetic flux. On the other hand, the direction of the discharge gas flow in the nonequilibrium atmospheric pressure plasma generator 10 is not parallel to the direction of magnetic flux, and forms a predetermined angle to the direction of magnetic flux. This prevents the discharge gas from entering the reaction chamber 23 through a window 53 disposed in the top surface of the case 27. In other words, the discharge gas does not prevent the plasma generated by the electrodes 32a and 32b from extending to the plasma-leading electrode 50. This structure allows the object to be efficiently irradiated with plasma, thus improving the atomization capability and the sensitivity of the component analysis.

Furthermore, the case 27 is provided with a gas inlet 54 and a gas outlet 55. The same gas as the discharge gas is supplied to the reaction chamber 23 to promote the generation of plasma in the reaction chamber 23. Alternatively, a gas containing a halogen element may be supplied to the reaction chamber 23 to convert a solid sample that is difficult to evaporate into a more volatile halide, thus promoting atomization. In all the Embodiments, the discharge gas may be argon, oxygen, nitrogen, helium, or another inert gas.

Modified Embodiment

Figure 13:
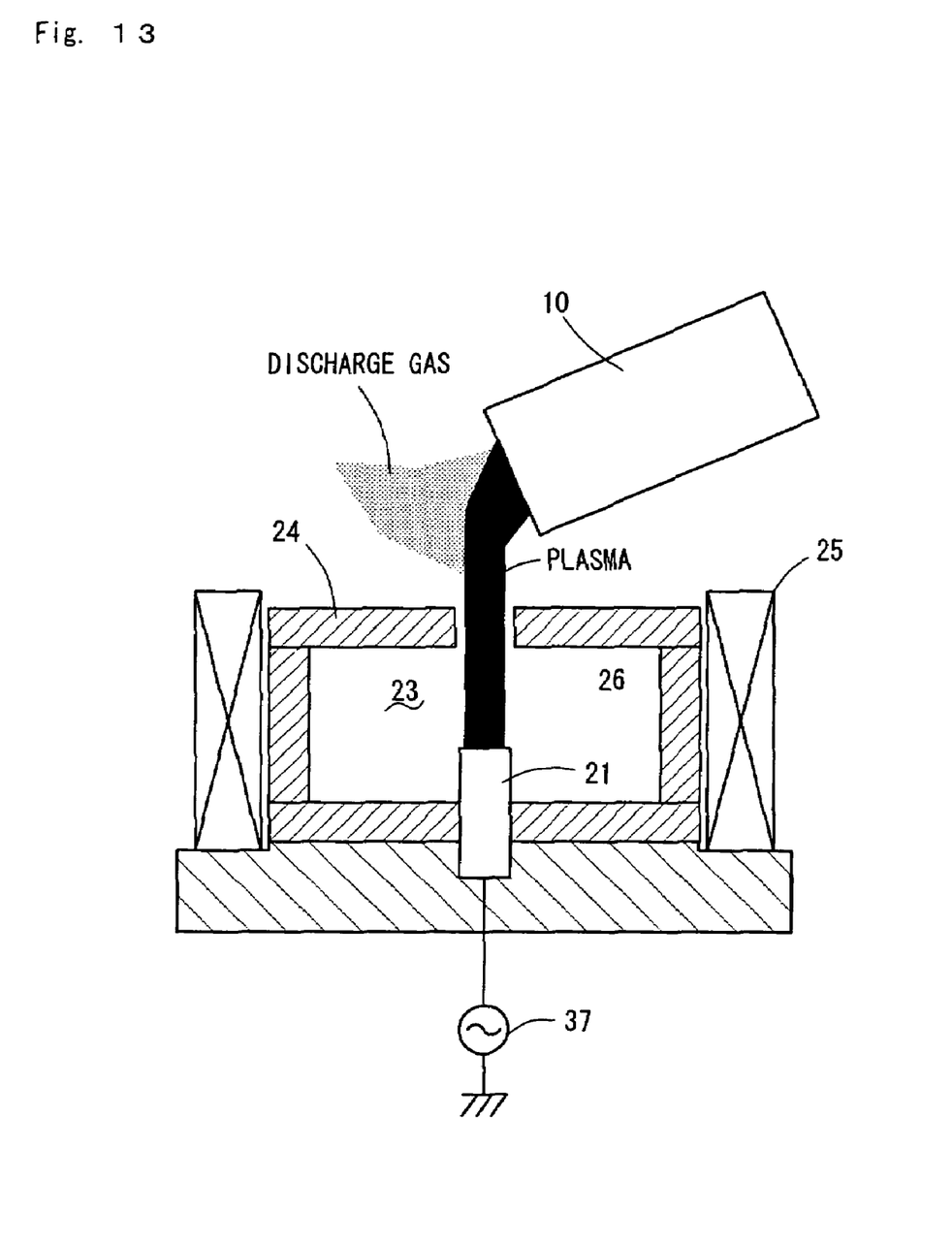
[FIG. 13] A schematic view of an atomic analyzer according to a modification of specific Embodiment 1 of the present invention.

As illustrated in FIG. 13, to prevent the discharge gas from entering the reaction chamber 23 in the apparatus described in Embodiment 1, the direction of the discharge gas flow may be altered to form a predetermined angle to the direction of magnetic flux rather than being the direction parallel to the direction of magnetic flux. Furthermore, while emission spectrometry is used in the Embodiments described above, another atomized environment may be irradiated with light from another light source, and absorption characteristics of the light may be analyzed to identify or quantitate an atom. In this case, as the light source, light may be produced by allowing a gas containing the same element as an atom to be analyzed to discharge electricity. That is, atomic absorption spectrometry may be performed.

In all the Embodiments, a bias voltage may be applied to a gas appropriately introduced to the reaction chamber 23 to promote the atomization of the object to be irradiated. For example, a gas containing a halogen element may be introduced to evaporate the object as a halide and atomize atoms composing the object.

INDUSTRIAL APPLICABILITY

The present invention can be utilized in an atomic analyzer that is effectively used to identify or quantitate metal atoms contained in sludge, waste fluid, soil, or the like. The present invention is effective to atomize an object to be irradiated, in particular, a solid element for the spectroscopic analysis of atoms.

REFERENCE NUMERALS 10 plasma generator
21 and 50 plasma-leading electrode
22 object to be irradiated
23 reaction chamber
24 wall
25 magnetic field generator
27 case
26, 28, and 53 window
29 plate for preventing the adhesion of impurities
30 insulating pipe
31a and 31b electrode
40 spectrometer
51 sample stage

The invention claimed is:
1. An atomic analyzer, comprising:
a plasma generator in which a discharge gas is fed in a micro gap between a pair of electrodes to generate nonequilibrium atmospheric pressure plasma;
a bias voltage controller that includes a plasma-leading electrode for leading the nonequilibrium atmospheric pressure plasma generated by the plasma generator to an object to be irradiated, the object to be irradiated with the nonequilibrium atmospheric pressure plasma being placed on the plasma-leading electrode, a bias voltage being applied between the plasma-leading electrode and the electrodes of the plasma generator to irradiate the object with the nonequilibrium atmospheric pressure plasma; and a spectrometer that analyzes the atoms spectroscopically from light emitted from atomized atoms generated by atomizing a substance composing the object to be irradiated by the nonequilibrium atmospheric pressure plasma irradiation or from light absorbed by said atomized atoms.

2. The atomic analyzer according to claim 1, further comprising a magnetic field generator that is disposed between the plasma-leading electrode and the electrodes of the plasma generator, confines the nonequilibrium atmospheric pressure plasma emitted to the object to be irradiated, surrounds the object to be irradiated, and applies a magnetic field to the object to be irradiated.

3. The atomic analyzer according to claim 2, wherein a flow direction of the nonequilibrium atmospheric pressure plasma emitted to the object to be irradiated is altered by a magnetic field generated by the magnetic field generator so that a direction of radiation of the nonequilibrium atmospheric pressure plasma is different from a flow direction of the discharge gas.

* * * * *